(12) United States Patent
Haven et al.

(10) Patent No.: US 7,280,678 B2
(45) Date of Patent: Oct. 9, 2007

(54) APPARATUS AND METHOD FOR DETECTING PUPILS

(75) Inventors: Richard Earl Haven, Sunnyvale, CA (US); David James Anvar, Sunnyvale, CA (US); Julie Elizabeth Fouquet, Portola Valley, CA (US); John Stewart Wenstrand, Menlo Park, CA (US)

(73) Assignee: Avago Technologies General IP Pte Ltd, Singapore (SG)

( * ) Notice: Subject to any disclaimer, the term of this patent is extended or adjusted under 35 U.S.C. 154(b) by 787 days.

(21) Appl. No.: 10/377,687

(22) Filed: Feb. 28, 2003

(65) Prior Publication Data

US 2004/0170304 A1   Sep. 2, 2004

(51) Int. Cl.
  *G06K 9/00*  (2006.01)
  *A61B 3/14*  (2006.01)
  *H04N 7/18*  (2006.01)
  *H04N 9/47*  (2006.01)

(52) U.S. Cl. .................... 382/117; 351/206; 348/78
(58) Field of Classification Search ........... 382/117; 351/206; 348/78
  See application file for complete search history.

(56) References Cited

U.S. PATENT DOCUMENTS

| | | | | |
|---|---|---|---|---|
| 3,795,444 A | * | 3/1974 | Glidden et al. | 355/68 |
| 5,016,282 A | * | 5/1991 | Tomono et al. | 382/117 |
| 5,204,703 A | * | 4/1993 | Hutchinson et al. | 351/210 |
| 5,359,669 A | * | 10/1994 | Shanley et al. | 382/117 |
| 5,422,690 A | * | 6/1995 | Rothberg et al. | 351/209 |
| 5,598,145 A | * | 1/1997 | Shimotani et al. | 340/576 |
| 5,905,563 A | | 5/1999 | Yamamoto | |
| 6,082,858 A | * | 7/2000 | Grace et al. | 351/200 |
| 6,353,494 B1 | * | 3/2002 | Hamada | 359/322 |
| 6,616,277 B1 | * | 9/2003 | Davenport | 351/221 |
| 6,714,665 B1 | * | 3/2004 | Hanna et al. | 382/117 |

(Continued)

FOREIGN PATENT DOCUMENTS

| | | |
|---|---|---|
| DE | 44 41 332 | 5/1995 |
| DE | 44 41 332 | * 5/1998 |
| DE | 197 19 695 | * 11/1998 |
| EP | 0 350 957 | 7/1989 |
| WO | WO 00/27273 | 5/2000 |

OTHER PUBLICATIONS

Ebisawa, Yoshinobu and Shin-ichi Satoh. "Effectiveness of Pupil Area Detection Technique using Two Light Sources and Image Difference Method". Proceedings of the 15th Annual International Conference of the IEEE Engineering in Medicine and Biology Society: 1993. vol. 15. pp. 1268-1269.*

(Continued)

*Primary Examiner*—Andrew W. Johns
*Assistant Examiner*—Damon M Conover

(57) ABSTRACT

Methods and apparatus for pupil detection are described. First light is emitted from a first light source at a first illumination angle relative to the axis of a detector. Second light is emitted from a second light source at a second illumination angle relative to the axis. The first light and the second light can have substantially equal intensities. The second illumination angle is greater than the first illumination angle. Reflected first light and reflected second light are received at the detector. The difference between the reflected first light and the reflected second light can be determined. The difference can be used to detect the pupils of a subject's eyes.

51 Claims, 7 Drawing Sheets

U.S. PATENT DOCUMENTS

| | | |
|---|---|---|
| 6,717,518 B1 * | 4/2004 | Pirim et al. ................. 340/576 |
| 6,734,911 B1 * | 5/2004 | Lyons ........................ 348/340 |
| 2003/0012413 A1 * | 1/2003 | Kusakari et al. ............ 382/117 |
| 2003/0118217 A1 * | 6/2003 | Kondo et al. ............... 382/117 |

OTHER PUBLICATIONS

Ebisawa, Yoshinobu. "Unconstrained Pupil Detection Technique using Two Light Sources and the Image Difference Method". Visualization and Intelligent Design in Engineering and Architecture: 1995. pp. 79-89.*

Shumin Zhai, et al.; "Manual and Gaze Input Cascaded Pointing"; IBM Almaden Research Center.

Carlos Morimoto, et al.; "Pupil Detection and Tracking Using Multiple Light Sources"; IBM Almaden Resaerch Center.

Erica Rowell; "Turned on and Jacked In"; ABCNews.com article; pp. 1-3.

Shumin Zhai, et al.; "Manual and Gaze Input Cascaded (Magic) Pointing"; IBM Almaden Research Center.

* cited by examiner

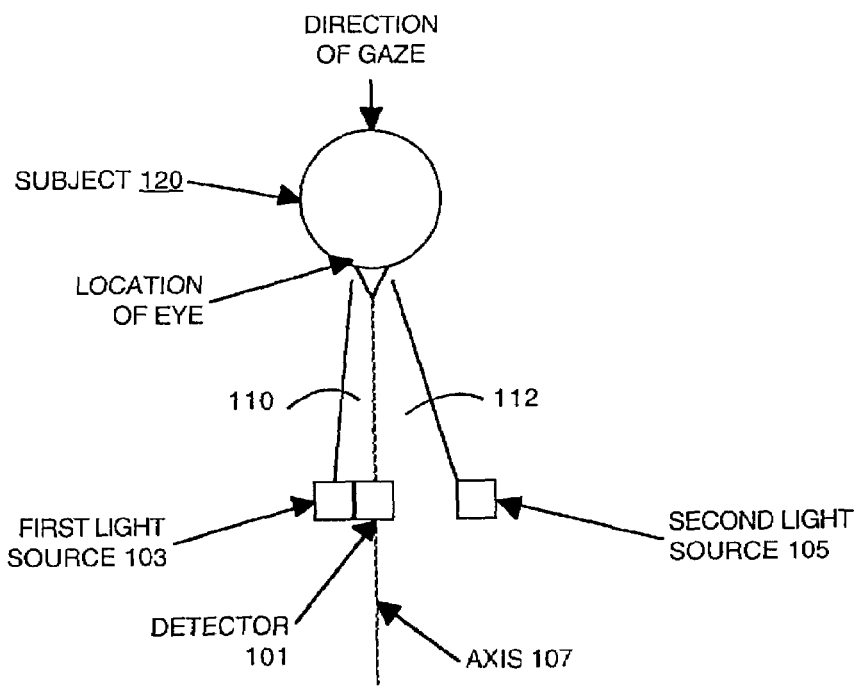
Figure 1
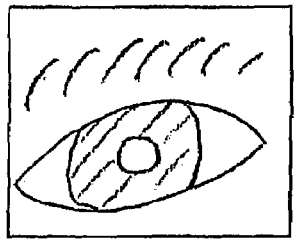
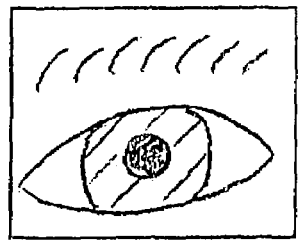
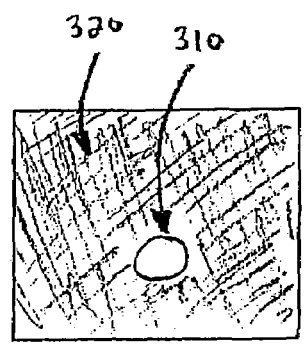
Figure 2A          Figure 2B          Figure 2C

APPARATUS AND METHOD FOR DETECTING PUPILS

TECHNICAL FIELD

Embodiments in accordance with the invention generally relate to the field of imaging. More specifically, embodiments in accordance with the invention relate to apparatus and methods for detecting the eyes of a subject.

BACKGROUND ART

There are a number of applications in which it is of interest to determine whether or not a person's eyes are open or closed as well as the amount of time that the eyes are open/closed. One such application is the detection of drowsiness in the operator of a motor vehicle, such as but not limited to the driver of an automobile or the like (e.g., a truck, etc., but also including airplanes, trains, etc.).

Prior art techniques have been developed to detect and monitor a person's eyes. Some of these techniques rely on the detection of light reflected off of the eye(s) of a subject. However, these techniques generally have one or more disadvantages that limit their use in motor vehicles. One disadvantage is their inability to provide reliable data. Another disadvantage is that they are typically invasive or distracting to the subject. For example, they may distract the subject while in operation, or it may be necessary for the subject to wear special equipment. Prior art techniques are also relatively complex in their setup and operation, perhaps requiring multiple specialized detectors and/or beam splitters, and perhaps requiring precision alignment of each of these parts. As such, the cost of prior art systems may be relatively high. If manufacturers and the public are to embrace drowsiness detectors, it is desirable for the detectors to be relatively unobtrusive and inexpensive.

Another disadvantage to prior art techniques is that they do not perform well during the day. Under brighter ambient light, the light reflected from the subject's eyes is relatively dim and hence more difficult to detect. Accordingly, the prior art techniques are not able to operate as efficiently or reliably during the day. In addition, at night, other light sources (such as headlights, streetlights, etc.) can interfere with detection of the light reflected from the subject's eyes. Thus, prior art techniques may be problematic at night as well as during the day.

Another prior art technique for drowsiness detection may be generally referred to as a lane change detector. This technique looks at the surface of the road (more specifically, at features of the road such as lane markers) to determine if the vehicle is drifting into another lane or off the road. One problem with this type of technique is that not all roads have the features relied upon (e.g., lane markers may be absent). Another problem arises because once the change in lanes is detected, there will likely be an immediate need for corrective action. In other words, a lane change detector may not anticipate that a problem (e.g., inappropriate lane change) is occurring, and instead will alert the driver only after the problem has occurred. By the time the lane change detector infers that the vehicle is drifting out of its lane, the operator may already be asleep and thus may not have the faculties needed to take immediate and proper corrective action.

DISCLOSURE OF THE INVENTION

The invention provides, in various embodiments, pupil detection apparatus and methods thereof. The locations of pupils as well as the amount of time that the eyes are open/closed/nearly closed can be determined in a non-invasive manner, without making physical contact with the subject. Pupils/drowsiness can be detected both in the dark and in the presence of background light at various levels, including bright light. Pupils/drowsiness can be detected for stationary subjects as well as moving subjects and backgrounds. The apparatus, in its various embodiments, can be located in a variety of locations relative to the subject. The use of infrared light in some embodiments will not interfere with the subject's night vision, and is invisible to most people. Setup and operation is simple, and the cost is low.

Besides drowsiness detection, embodiments in accordance with the invention can be used to: monitor the onset or the end of sleep; detect drowsiness in venues other than motor vehicles; detect the level of attentiveness of a subject, the presence of a subject, the location of a subject; locate the pupils for iris identification techniques; or measure pupil size. Other applications include lie detection and ophthalmology. Applications also include eye-based and facial-based biometric applications, such as eye or facial based identification applications including retinal detection and iris detection, or for distinguishing a live subject from an image of the subject. Applications may also include those for animal subjects.

BRIEF DESCRIPTION OF THE DRAWINGS

The accompanying drawings, which are incorporated in and form a part of this specification, illustrate embodiments of the invention and, together with the description, serve to explain the principles of the invention. The drawings referred to in this description should not be understood as being drawn to scale except if specifically noted.

FIG. 1 is a block diagram of one embodiment of an apparatus for pupil detection in accordance with the invention.

FIG. 2A illustrates an image generated with an on-axis light source according to one embodiment in accordance with the invention.

FIG. 2B illustrates an image generated with an off-axis light source according to one embodiment in accordance with the invention.

FIG. 2C illustrates an image resulting from the difference between the images from the on-axis and off-axis light sources according to one embodiment in accordance with the invention.

DETAILED DESCRIPTION OF THE INVENTION

Figure 3:
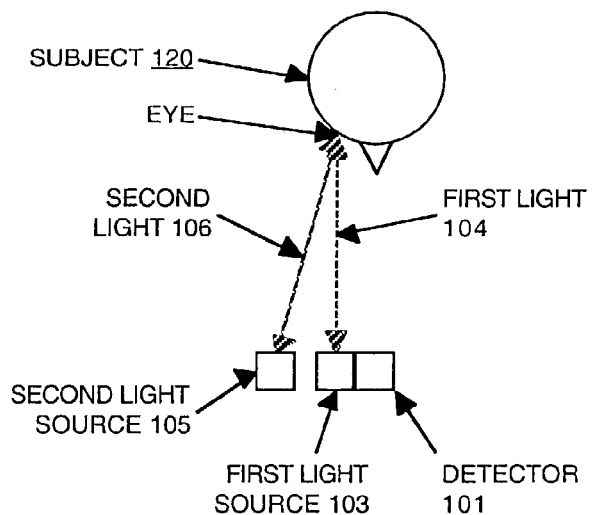
FIG. 3 is a block diagram showing the embodiment of FIG. 1 in operation according to one embodiment of the invention.

Reference will now be made in detail to the various embodiments in accordance with the invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. In other instances, well-known methods, procedures, components, and circuits have not been described in detail as not to unnecessarily obscure aspects of the present invention.

Illuminating Angle Differencing

Embodiments in accordance with the invention pertain to apparatus and methods for detecting whether or not a subject's eyes are open or closed. This information can be used, for example, to determine whether the operator of a motor vehicle is falling asleep and to sound an alarm should the operator appear to be doing so. In general, according to one embodiment in accordance with the invention, two images are taken of the subject's face (in particular, the subject's eyes are imaged) using some type of detector or imager. One of the images is taken using lighting that is close to or on the axis of the detector ("on-axis"), while the other image is taken using lighting that is a larger angle to the detector ("off-axis"). When the subject's eyes are open, the difference between the images will highlight the pupils of the eyes because the somewhat diffuse reflection from the retinas is detected only in the on-axis image (the strong pupil signal in the on-axis case is known as "red-eye" in conventional flash photography). Other facial and environmental features are largely cancelled out, leaving the pupils as the dominant feature in the differential image. When the pupils are not detectable in the differential image, then the subject's eyes are inferred as being closed. The amount of time that the subject's eyes are open or closed can be monitored against a threshold, for example. Should the threshold not be satisfied (e.g., should the percentage of time that the eyes are open fall below the threshold), an alarm or some other action can be taken to alert the subject. Other metrics, such as the frequency of blinking, can also be used.

The discussion above describes the monitoring of retinal reflection to determine the amount of time that a subject's eyes are open or closed. However, the amount of light reflected off the retina is also a function of the degree to which the subject's eyelids are closed; for example, reflection may be undetectable when the subject's eyes are drooping or the subject is squinting. Both of these factors—the amount of time the eyes are opened/closed, and the amount of time that the eyes are nearly closed—have been correlated to fatigue or sleepiness. The techniques described herein can be used to assess either of these factors: the subject's eyes are closed, and the subject's eyes are nearly closed.

Also, features in accordance with the invention are described primarily in the context of drowsiness detection. However, as will be seen, there are other applications in which the invention, in its various embodiments, may be utilized.

FIG. 1 is a block diagram of one embodiment of an apparatus for pupil detection in accordance with the invention. In this embodiment, the apparatus includes a detector 101 (e.g., an imaging detector), a first light source 103, and a second light source 105. The apparatus can optionally incorporate a controller or processor (e.g., an image processor), or instead it may be coupled to an external controller or processor. The drawings referred to in this description should be understood as not being drawn to scale.

For clarity of illustration, first light source 103 and second light source 105 are shown as being on opposite sides of detector 101; however, it is appreciated that they may instead be on the same side of detector 101. It is understood that a key principle in obtaining differential reflectivity off the retina is the dependence of retinal reflectivity on the angle between the source and the detector (this angle may be referred to as the illumination angle). Position of a light source with respect to the image sensor is subject to additional conditions. To achieve successful differencing of the images resulting in spots corresponding to the reflecting retina, it is desirable for the remainder of the field of view (including the subject's face, apparel and the interior of the vehicle) to have significantly similar illumination profiles under the two different angles of illumination. For example, it is undesirable for illumination from a single-side on-axis light source to produce shadows that are significantly different than the shadows produced by a second off-axis source. With the above information in mind, it is recognized that placing first and second light sources 103 and 105 on the same side of detector 101 has advantages over placing the light sources on opposite sides of the detector.

In the present embodiment, first light source 103 is situated at a first angle 110 from the axis 107 of detector 101, and second light source 105 is situated at a second angle 112 from the axis 107 (these angles are not drawn to scale). The angles 110 and 112 may be referred to as illumination angles. In general, a smaller first angle 110 will increase the retinal return. As used herein, the "retinal return" refers to the intensity—the real photon count or equivalent—that is reflected off the back of the subject's eye and back to the detector. The term "retinal return" is also used to include reflection off other tissue, etc., at the back of the eye (other than or in addition to the retina). Accordingly, first angle 110 is selected such that first light source 103 is on or close to axis 107. In one embodiment, first angle 110 is in the range of approximately zero to three (3) degrees.

In general, the size of second angle 112 is chosen so that only low retinal return from second light source 105 will be detected at detector 101. The iris (surrounding the pupil) blocks this signal, and so it is important to consider pupil size under different lighting conditions when selecting the size of second angle 112. Second angle 112 is larger than first angle 110; however, second angle 112 should not be too much larger than first angle 110 so that, with the exception of the pupil, an image captured using second light source 105 will be similar to an image captured using first light source 103. Accordingly, in one embodiment, second angle 112 is in the range of approximately 3 to 15 degrees. It is appreciated that the angles 110 and 112 (or equivalently, the positions of light sources 103 and 105) may be adjusted to suit, for example, the traits of a particular subject.

The first light source 103 can be referred to as being on-axis and the second light source 105 can be referred to as being off-axis. In one embodiment, the light sources 103 and 105 are light-emitting diodes (LEDs); however, the invention is not so limited. In another embodiment, detector 101, first light source 103, second light source 105, and axis 107 are situated in the same plane (or nearly so); however, the invention is not so limited. In practice, each light source described (for example, first light source 103) may be more than one light-emitting device, where each such device is located at substantially the same illumination angle. Additionally, some or all of the light sources may be vertical cavity surface-emitting lasers (VCSELs), with suitable diffusers if needed to widen the angle of illumination.

In one embodiment, the first light source 103 and the second light source 105 emit light that yields substantially equal image intensity (brightness), aside from the retinas. Light sources 103 and 105 may emit light of different or of substantially the same wavelengths; this is described further in conjunction with FIGS. 3, 6 and 7A–7D, below. The wavelength(s) and/or illumination intensities of light emitted by light sources 103 and 105 are selected so that the light will not distract the subject and so that the iris of the subject's eyes will not contract in response to the light; however, the selected wavelength(s) should be short enough for the detector 101 to respond (it is noted that imagers with thicker absorber regions tend to have better long-wavelength response). In one embodiment, infrared or near-infrared wavelengths are used by light sources 103 and 105.

FIG. 2A illustrates an image (specifically, an eye that is open) generated using an on-axis light source (e.g., first light source 103 of FIG. 1) according to one embodiment in accordance with the invention. The image of FIG. 2A illustrates a bright pupil due to a strong retinal return. If the eye had been closed (or perhaps nearly closed), the bright pupil would not be detected and imaged.

FIG. 2B illustrates an image (specifically, an eye that is open) generated using an off-axis light source (e.g., second light source 105 of FIG. 1) according to one embodiment in accordance with the invention. The image of FIG. 2B may be taken at the same time as the image of FIG. 2A, or it may be taken in a frame immediately adjacent to the image of FIG. 2A (e.g., 1/30th of a second ahead of or behind the image of FIG. 2A). The image of FIG. 2B illustrates a dark (that is, normal) pupil. If the eye had been closed or nearly closed, because of the proximity in time to the image of FIG. 2A, the image of FIG. 2B would likely also not show a bright pupil.

FIG. 2C illustrates an image resulting from the difference between the images generated using the on-axis and off-axis light sources (the images of FIGS. 2A and 2B, respectively) according to one embodiment in accordance with the invention. By taking the difference between the images of FIGS. 2A and 2B, a relatively bright spot 310 will remain against the relatively dark background 320 when the eye is open. There may be vestiges of other features of the eye remaining in the background 320; however, in general, the bright spot 310 will stand out in comparison to the background 320. When the eye is closed or nearly closed, there will be no bright spot in the differential image.

FIGS. 2A, 2B and 2C focus on one eye of the subject. It is appreciated that both eyes may be monitored as well. It is also appreciated that a similar effect will be achieved if the images include other features of the subject (e.g., other facial features) as well as features of the subject's environment (e.g., background, portions of the motor vehicle surrounding the vehicle operator, etc.). These other features will largely cancel out in a manner similar to that just described, leaving either a bright spot when the eye is open (or two bright spots, one for each eye), or no such spot(s) when the eye is closed or nearly closed.

In one embodiment, detector 101 utilizes a charge-coupled device (CCD) imager, while in another embodiment, detector 101 utilizes a complementary metal-oxide semiconductor (CMOS) imager, although the invention is not so limited. It is worth noting that, in general, CMOS imagers are less expensive than CCD imagers, and that CMOS devices in some cases provide better sensitivity at infrared/near-infrared wavelengths than CCD imagers.

In FIG. 1, the subject 120 is illustrated as directly facing the detector 101. However, subject 120 may face in other directions relative to detector 101. The angle formed between the direction in which subject 120 is looking and the axis 107 may be referred to as the gaze angle. The previously defined angles 110 and 112 do not change with gaze angle. The sensitivity of the retinal return to gaze angle is relatively weak. As such, the head and the eyes of subject 120 may frequently move relative to detector 101 and light sources 103 and 105, without significantly affecting the efficiency and reliability of the drowsiness detection apparatus.

The detector 101 and the light sources 103 and 105 can be located at virtually any distance from the subject 120 within the motor vehicle. The detector 101 and light sources 103 and 105 provide satisfactory coverage of the area within the motor vehicle in which the subject 120 is typically seated. Of course, if the subject 120 is facing away from the drowsiness detection apparatus, a retinal return will not be detected. If the aforementioned open-eye threshold is not satisfied, an alert is made (e.g., sounded).

FIG. 3 is a block diagram showing the embodiment of FIG. 1 in operation according to one embodiment in accordance with the invention. First light 104 is emitted from first light source 103 and is reflected from subject 120 back to first light source 103. Second light 106 is emitted from second light source 105 and is reflected from subject 120 back to second light source 105.

It is appreciated that, in the present embodiment, the light is "broadcast" onto the face of subject 120 (as well as portions of the surrounding environment). For clarity of illustration, a single beam of light is shown as being emitted from light sources 103 and 105, although in the present embodiment the light is actually diffuse. In another embodiment, a relatively directed beam of light, such as that emitted by a laser, could instead be used, recognizing that it is important that the light not distract the vehicle operator. A diffuser may be used with the laser to illuminate the vehicle operator.

According to the present embodiment, a strong retinal return will be provided to detector 101 by first reflected light 104 but not by second reflected light 106. The difference between the first reflected light 104 and the second reflected light 106 (or the difference between the frames so generated) will indicate the pupil(s) of the eye(s) of subject 120, provided the eyes are sufficiently open.

Continuing with reference to FIG. 3, in the present embodiment, the light from light sources 103 and 105 is emitted in pulses that are typically synchronized with the frame rate of detector 101. For example, if detector 101 operates at a frame rate of 30 frames per second (fps), then the light is emitted at a rate of 30 pulses per second. In one embodiment, the pulses of light from light sources 103 and 105 are not continuously emitted, but instead are emitted (e.g., pulsed) in bursts with a period that is longer than the bursts. For example, for a frame rate of 30 fps, four pulses of light may be emitted over 4/30th of a second, with no light pulses emitted over the remaining 26/30th of a second. In this manner, sufficient information is collected to determine whether the subject's eyes are open or closed (or nearly closed), while the potentials for eye exposure and distracting the operator are reduced.

It is appreciated that frame rates other than 30 fps may be used; for example, higher frame rates are expected to reduce artifacts resulting from the motion of subject 120 (e.g., the vehicle operator) or from background motion.

Sequential Imaging

The light from light sources 103 and 105 may or may not be of essentially the same wavelength. In an embodiment in which the light emitted from light sources 103 and 105 is essentially the same wavelength, it may be emitted at different times. That is, for example, a pulse is emitted from light source 103, followed by a pulse from light source 105, and so on for the length of the burst (as described above). It is, in general, desirable for the light sources 103 and 105 to alternate emitting light pulses, one pulse at a time, in order to generate consecutive on-axis and off-axis frames. For example, even-numbered frames can be associated (synchronized) with first light source 103, and odd-numbered frames can be associated with second light source 105. Consecutive frames will be generated very close in time to each other (e.g., within about 1/30th of a second). As such, the frames will be very similar, reducing motion artifacts and thereby facilitating the process of finding the difference between any two consecutive frames.

Timing for Sequential Imaging

Figure 4A:
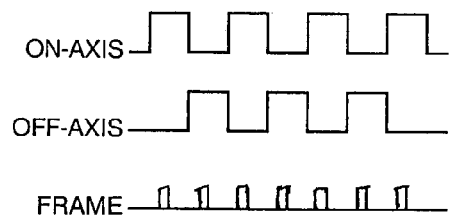
FIGS. 4A and 4B illustrate various timing options between the light source(s) and the detector according to various embodiments in accordance with the invention.
Figure 4B:
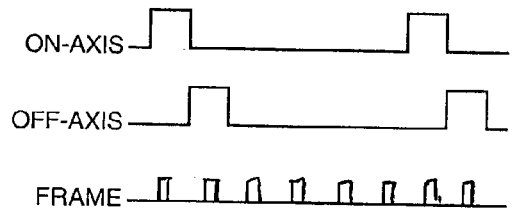

For sequentially-acquired images, FIGS. 4A and 4B illustrate different relationships between the timing of the pulses emitted by the on-axis and off-axis light sources (e.g., first light source 103 and second light source 105, respectively, of FIG. 1) and the frame rate, according to embodiments in accordance with the invention. As used herein, "frame rate" refers to the inverse of a "frame cycle," where frame cycle refers to the time to return to the same point in the data output sequence. During a frame cycle, data may be captured and read out only for subsets of the cycle.

In FIG. 4A, the pulses are alternately emitted by the on-axis and off-axis light sources, one pulse per frame. In FIG. 4B, a pulse is emitted by the on-axis light source, then a pulse is emitted by the off-axis light source (or vice versa), one pulse per frame; the lights are then turned off (no pulse is emitted) for a number of frames, and the process is repeated.

It is appreciated that other options are available for timing the light sources with respect to the frame rate. These options include: one or more lights sources always on; a single pulse (from a single source) per frame; a single pulse (from a single source) extending over multiple frames; a single pulse (from a single source) lasting only a fraction of a frame; pulses that are offset from the frames; pulses that skip frames before the pattern of pulses is repeated (e.g., for modulation); combinations of the above; and variations on the above that can be derived from those of skill in the art.

Simultaneous Imaging

In order to eliminate motion artifacts, the two images can be collected simultaneously if they can be distinguished by some optical property such as wavelength or polarization. For example, if the light emitted from first light source 103 is at a different wavelength from the light emitted from second light source 105, the light may be emitted at essentially the same time. In one such embodiment, the wavelength that yields the strongest retinal return is used by first light source 103 (the light source closest to detector 101), and the other of the two wavelengths is used by second light source 105 (the light source furthest from detector 101). Measured on a conventional silicon-based detector, the retinal return signal is typically stronger at 800 nano-meter (nm) wavelengths versus 950 nm wavelengths, and it is therefore desirable to associate the shorter wavelength with the on-axis light source in this case.

When light is emitted from both light sources 103 and 105 at essentially the same time, the on-axis and off-axis frames will be acquired at essentially the same time by detector 101. By acquiring both the on-axis and off-axis frames at essentially the same time, motion artifacts can be eliminated and timing constraints placed on detector 101 can be relaxed. Furthermore, the timing between consecutive measurement cycles is less critical. Consequently, the time between consecutive measurement cycles can be increased (e.g., it can be greater than 1/30th of a second), although it is important that the time between consecutive measurement cycles be short enough to still acquire a sufficient amount of data (in essence, to continuously monitor the vehicle operator). For example, images can be acquired once per second instead of four times per second. The advantages of this include increased sensitivity to the captured images, reduced image handling capacity, lower costs, and/or decreased exposure of the subject.

Using different wavelengths for light sources 103 and 105, the on-axis and off-axis frames can be acquired in various ways. Some of these methods use bulk optics, while others use sensors with pixel-based filters.

Bulk Methods for Simultaneous Imaging

In order to collect two images simultaneously, light from the two sources must be distinguished somehow. Two means of separation are wavelength and polarization. Two types of sources can be selected to represent the on-axis and off-axis sources, where one type of source is used in the on-axis positions and a complementary type of source is used in the off-axis positions. In one embodiment, light collected from the subject passes through a beam splitter. For example, this beam splitter may transmit half of the incident light and reflect the other half. The reflected portion is directed onto one detector, while the transmitted portion is directed onto another detector. In practice, other splitting ratios may be used. A ratio that compensates for differences in sensitivity between the two imaging channels may be other than a 50/50 split. In the case of wavelength separation, wavelength-selective filters can be positioned in front of the two detectors, so that the on-axis light is transmitted to one detector but not the other. Off-axis light is transmitted to the other detector. Alternatively, the wavelength filtering function can be incorporated in the beam splitter. Such a dichroic beam splitter would transmit one wavelength and reflect the other.

An alternative geometry uses two adjacent imagers, each preceded by an appropriate wavelength-selective filter. In this case, it would be desirable to package the imagers in the same carrier to reduce separation as much as possible. An appropriate bulk filter can be positioned over each imager.

Figure 5:
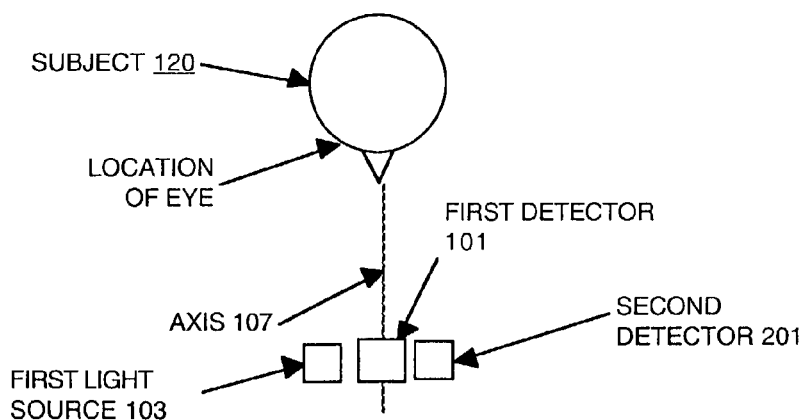
FIG. 5 is a block diagram of one embodiment of an apparatus for pupil detection in accordance with the invention.

In another embodiment, shown in FIG. 5, a second detector 201 is used without a beam splitter. The functionality of second detector 201 is similar to that described for first detector 101 in the discussion of FIGS. 1 and 3, above. Using only the first light source 103, on-axis and off-axis illumination views are possible using detectors 101 and 201. Furthermore, the detectors 101 and 201 can be synchronized using well known techniques to simultaneously capture images and reduce motion artifacts in the difference image.

Polarization is an alternative basis for separating the two signals. In one embodiment, one type of source would be polarized in one direction while the other type of source would be polarized in an orthogonal direction. Appropriate polarizers would be positioned in front of the imagers, or a polarizing beam splitter can be used if a beam splitter embodiment is used. Detection at the appropriate polarization may additionally improve signal-to-interference ratios because scattered sunlight from the outdoor environment is polarized. In another embodiment, a single polarized light source may be utilized, and different facial features may be detected through their differential responses, e.g., showing the extent to which light is depolarized when it scatters off those features.

Pixel-Based Methods for Simultaneous Imaging

In order to reduce costs as much as possible, interleaving the filtering function on the surface of one imager is desirable. Furthermore, this approach provides advantages with regard to the relative aim between the two output imaging channels and the time synchronization. Microfilters or polarizers can be patterned on the surface of an imager in a checkerboard pattern in order to interleave the filtering function on the surface of an imager.

Figure 6:
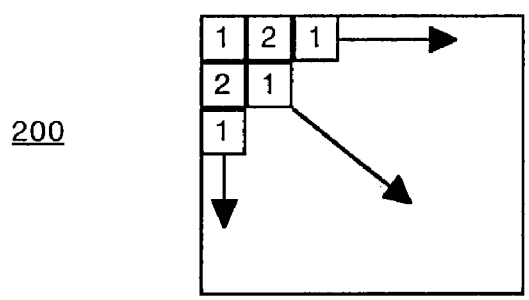
FIG. 6 illustrates one embodiment of an imaging device used in accordance with the invention.

In the embodiment of FIG. 6, a checkerboard pattern is formed on the sensor 200 using two types of filters according to the wavelengths being used by light sources 103 and 105 (FIG. 3). That is, for example, sensor 200 includes regions (identified as 1) that include a filter material for filtering the first wavelength, and other regions (identified as 2) that include a filter material for filtering the second wavelength. In the present embodiment, sensor 200 is incorporated into detector 101 (FIG. 1). It is appreciated that the different filter materials can be arrayed in a pattern other than a checkerboard pattern. The filter materials can be deposited (e.g., layered) as a separate layer of sensor 200 (e.g., on top of an underlying layer) using conventional deposition and photolithography processes while still in wafer form, reducing the cost to manufacture. Additionally or alternatively, the filter materials may be mounted as separate elements between the sensor 200 and incident light, allowing bulk or uniform filtering of light before the light reaches the surface of sensor 200.

In another embodiment, one of the two filter materials can be patterned onto the imager in wafer form while a complementary large area filter blankets the entire imager. Various types of filters can be used for the small and large filters, including polymers doped with pigments or dyes, interference filters, reflective filters, and absorbing filters made of semiconductors, other inorganic materials, or organic materials. In yet another embodiment, the wavelength and/or gain sensitivity may be varied within the silicon pixels themselves in a checkerboard pattern, for example.

Similarly, polarization-sensitive detection can be used to distinguish the signals from the two different illumination angles. Polarizers for simultaneous capture may be fabricated as parallel thin metallic strips over sensors. The strips on a given pixel would be oriented orthogonal to the strips on the adjacent pixels, so that adjacent pixels would detect orthogonal polarizations. These metallic strips may be fabricated using semi-transparent materials, for example indium tin oxide.

Wavelength Crosstalk Considerations

In order to avoid wavelength crosstalk, it is desirable that the pigmented polymer used for selecting the off-axis wavelength not transmit radiation at the on-axis wavelength. Crosstalk in the opposite direction is not as detrimental because of the strength of the on-axis retinal return at the on-axis wavelength. The angle dependence of the retinal return is much stronger than the wavelength dependence, so that different wavelengths that each provide a strong retinal return may be used for light sources 103 and 105. This approach has the advantage of simplifying filter requirements. For example, a long wavelength-pass filter can be used to block visible light from all pixels. This filter may be either a bulk filter in front of the imager chip or it may be a film blanketing the imager chip. An additional filter can be deposited on half the pixels, for example in a checkerboard pattern. This filter could be a long wavelength-pass filter which blocks the shorter wavelength but passes the longer wavelength.

Figure 7A:
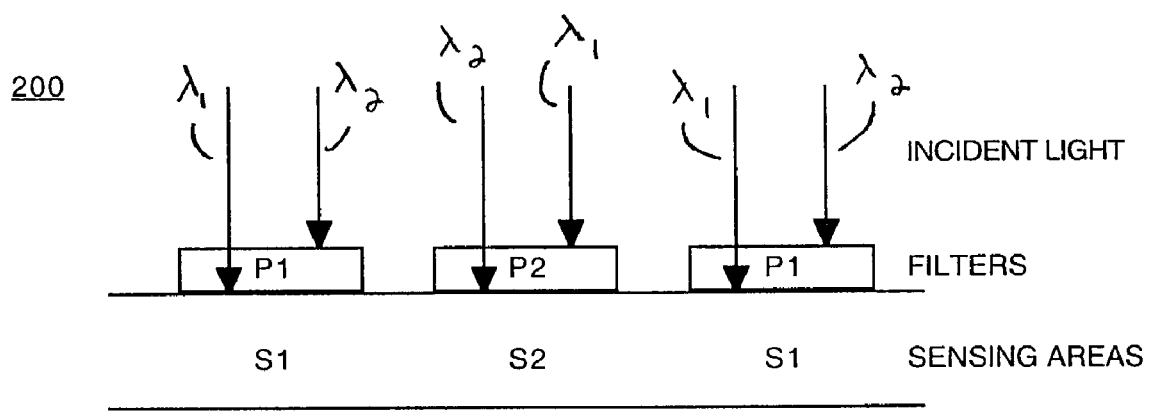
FIGS. 7A, 7B, 7C and 7D illustrate additional details of the imaging device of FIG. 6 according to various embodiments in accordance with the invention.
Figure 7B:
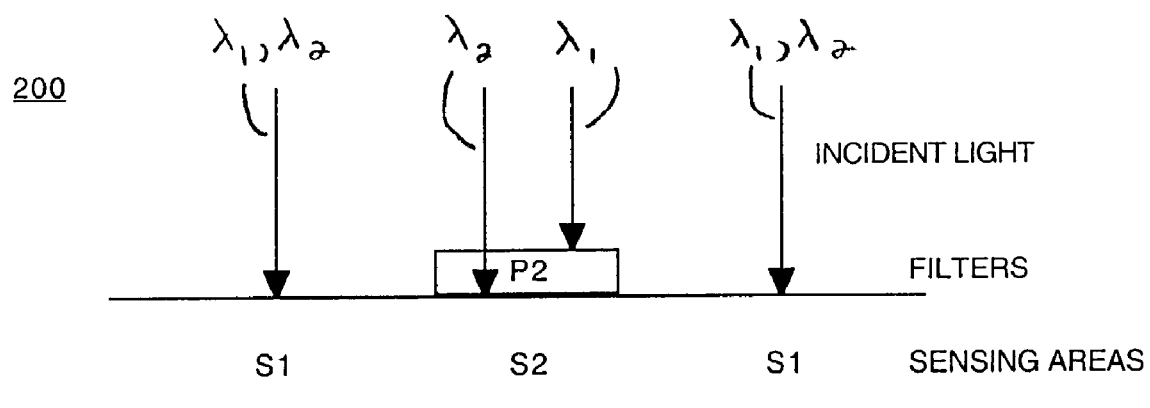

FIGS. 7A and 7B are cross-sectional diagrams illustrating embodiments of the sensor 200 that may be used according to the various embodiments in accordance with the invention. Only a portion of the sensor 200 is illustrated in these figures. With reference first to FIG. 7A, sensing areas S1 are for detecting light at a first wavelength ($\lambda_1$), and sensing areas S2 are for detecting light at a second wavelength ($\lambda_2$). The filters P1 and P2 can be inorganic films, polymer films, vapor-deposited films, etc. The filters P1 and P2 each have different transmission properties for filtering out light at the second and first wavelengths ($\lambda_2$ and $\lambda_1$, respectively). For example, polymer films may use different pigments or dyes, and inorganic films may use thin metal layers, semiconductor materials, or dielectric materials.

With reference to FIG. 7B, a filter (e.g., P2) is disposed over one set of sensing areas (e.g., S2), allowing light of a second wavelength ($\lambda_2$) to be sensed at both sensing areas S1 and S2, while allowing light of a first wavelength ($\lambda_1$) to be sensed at sensing areas S1 but not at sensing areas S2.

Figure 7C:
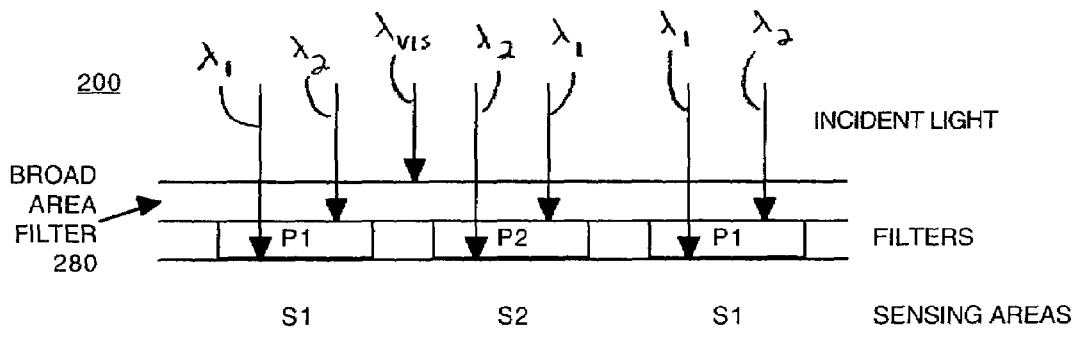
Figure 7D:
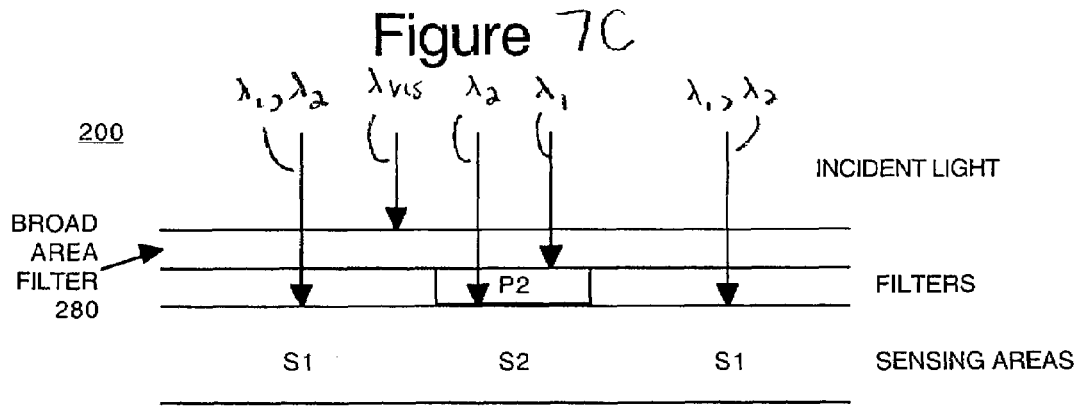

FIGS. 7C and 7D illustrate additional embodiments of sensor 200 in which a broad area filter 280 is mounted over the filters P1 and P2, for blocking visible light ($\lambda_{VIS}$) from the sensing areas S1 and S2.

Alternative Geometries

Figure 8:
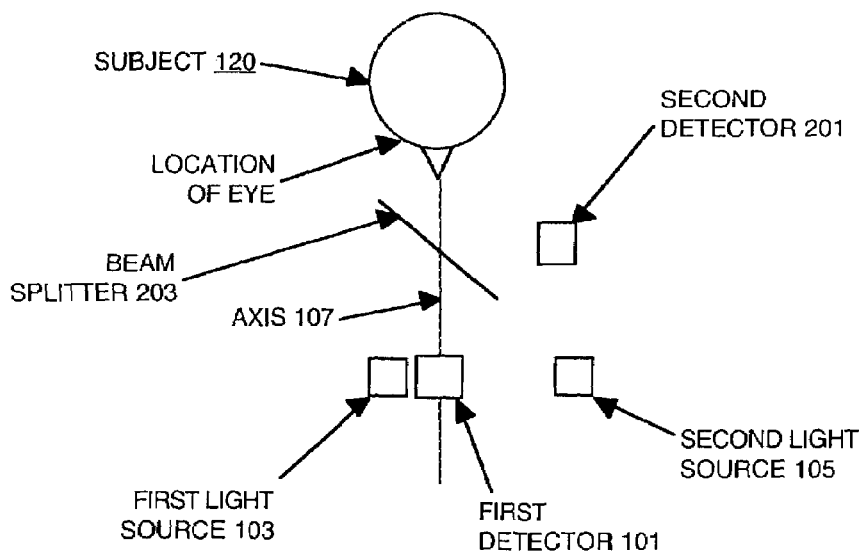
FIG. 8 is a block diagram of one embodiment of an apparatus for pupil detection in accordance with the invention.

FIG. 8 is a block diagram of another embodiment of an apparatus for pupil detection in accordance with the invention. In this embodiment, first light source 103 uses one wavelength, second light source 105 uses another (different) wavelength), and a second detector 201 (e.g., an imaging detector) is used with a beam splitter 203. Beam splitter 203 (e.g., a dichroic beam splitter), in conjunction with wavelength-selective filter elements, directs reflected light of one wavelength to first detector 101 and directs reflected light of the other wavelength to second detector 201.

Figure 9:
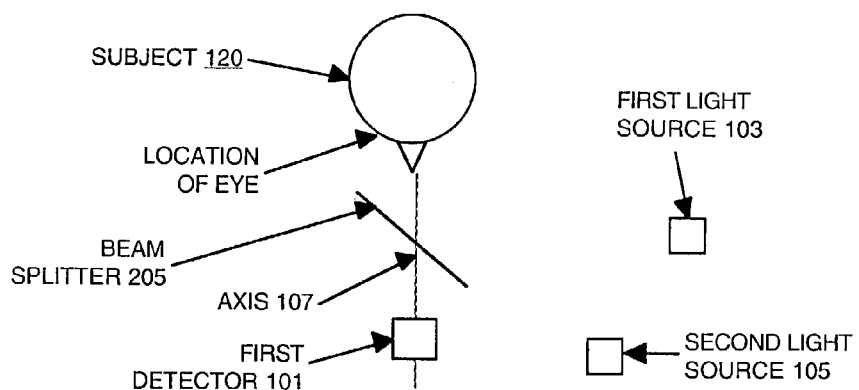
FIG. 9 is a block diagram of one embodiment of an apparatus for pupil detection in accordance with the invention.

FIG. 9 is a block diagram of yet another embodiment of an apparatus for pupil detection in accordance with the invention. In this embodiment, a portion of the light from first light source 103 is reflected by beam splitter 205 (e.g., a 50/50 beam splitter) onto subject 120 along the axis 107 (the remainder of the light from first light source 103 passes through beam splitter 205). Light reflected from subject 120 will travel along axis 107; a portion of the light along axis 107 will pass through beam splitter 205 to detector 101. Thus, in this embodiment, the first light source 103 is, in operation, essentially on-axis (on the detector axis).

Figure 10:
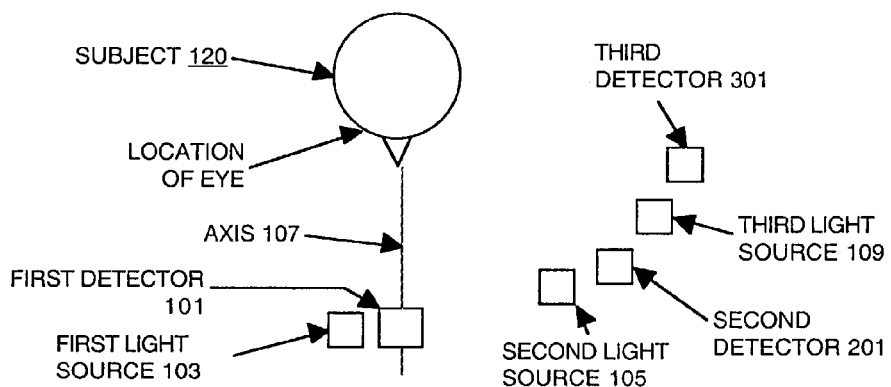
FIG. 10 is a block diagram of one embodiment of an apparatus for pupil detection in accordance with the invention.

FIG. 10 illustrates another embodiment of a pupil detection apparatus in which a third detector 301, similar in functionality to 101 and 201, is placed further off-axis. There may also be additional light sources 105 and 109. Generally, locating each additional light source close to its respective detector is desirable, in order to provide on-axis illumination for the respective source/detector pair. This may be relaxed by using multiple light detectors with a single light source, as shown by FIG. 5. A particular set of light sources and detectors (e.g., those that give best results) can be selected, thereby allowing flexibility in the initial setup.

Multiple sources and detectors can increase the range of gaze angle for detecting pupils, reduce instances when the pupils are obstructed (such as by the nose, by glare off of eyeglasses, or by eyeglass frames), accommodate a wider range of individuals and individual head positions without repositioning the detectors and sources, and provide hardware redundancy. One example is to use the combination of detector 101 with light sources 103 and 105 that has been described above. Alternatively, detector 301 can be used with light sources 105 and 109; detector 101 can be used with light sources 103 and 109; or detectors 201 and 301 can be used with light source 105. These are only a few of the possible combinations. The particular combination being used may change over time as ambient lighting and the subject's head position or eyewear changes. It is further understood that using multiple detectors and light sources is not limited to the specific configurations described herein. More than three detectors or light sources are extensions of the above concept. It is also possible to have some detectors or light sources at one wavelength, and others at another wavelength.

In other embodiments, a single detector may be used with three light sources. In one such embodiment, the first light source is on-axis with the detector, and the second and third light sources are at two different off-axis angles from the detector. In this embodiment, the first and second light sources can be used in sequence to obtain one difference image, and the first and third light sources can be used to obtain a separate difference image. The use of these separate difference images facilitates discrimination between the retinal return and glare. Generally, the retinal return will be nearly the same in the separate difference images, whereas glare will not always be the same because the glare under illumination with the second light source will not necessarily be the same as glare under illumination with the third light source.

In another embodiment using a single detector with three light sources, the first light source is on-axis with the detector, and the second and third light sources are at two different off-axis angles from the detector. In this embodiment, the first source has a wavelength $\lambda_1$, and the second and third light sources have substantially different wavelengths $\lambda_2$ and $\lambda_3$, respectively. With this embodiment, a single image can be collected with a three "color" wavelength discriminating sensor. Two distinct difference images—one between wavelengths $\lambda_1$ and $\lambda_2$ and the other between wavelengths $\lambda_2$ and $\lambda_3$—can be digitally processed. These two distinct images can be used as described above to facilitate discrimination between the retinal return and glare. This embodiment offers an advantage over single wavelength embodiments in that only a single image is acquired in order to process the difference images, thereby virtually eliminating motion artifacts.

In yet another embodiment using a single detector with three light sources, the first light source is on-axis with the detector, and the second and third light sources are at two different off-axis angles from the detector. In this embodiment, two of the three sources have the same wavelength. In this embodiment, two images are acquired. One image is acquired with a single light source with wavelength $\lambda_1$. The second image is acquired with the other two light sources simultaneously illuminated, one light source with wavelength $\lambda_1$ and the other with a different wavelength $\lambda_2$. The two images can be digitally processed to produce two distinct difference images that can be used as described above to facilitate discrimination between the retinal return and glare. This embodiment is expected to be easier and less expensive to fabricate than the three-wavelength embodiment above.

Eye-Based Biometric Applications Using Differential Illumination Imaging

Another way to achieve simultaneous images is to use either second detector 201 or a mosaic color filter portion of a single imager as a conventional visible color imager. Because the eye detection techniques described here utilize the three-dimensional aperture properties of the eye, this technique can be used to distinguish live human eyes from photographs thereof. This capability increases the security of eye-based and facial-based identification systems against intruders. This differential angle imaging technique can also be used to find pupils within a field of view, which can then be identified using an eye-based identification technique such as iris detection or retinal detection in the visible and/or near-infrared wavelengths.

In one embodiment, biometric identification can be provided using one imaging detector, while a second imaging system such as one of those described here verifies the three-dimensional properties of a live human's eye. As used herein, "biometric" refers to any specific and uniquely identifiable physical human characteristic, for example, the retina, iris, acoustic spectrum of the voice (e.g., voiceprint), fingerprint(s), handwriting, pattern of finger lengths, etc., that may be used to validate the identity of an individual. Accordingly, features of the invention can be used to distinguish a live subject from an image (e.g., a photograph) of the subject. Alternatively, an imager for reliable iris detection might use a mosaic with infrared and perhaps visible filters applied to individual pixels, that locates pupils using differential angle imaging as described above, then applies iris identification techniques such as those that use rapid video analysis of iris texture (e.g., the iris identification technique of John Daugman). In one embodiment, a higher-resolution imager may be pointed at the pupils once they have been located in a larger field of view by a lower-resolution imager. For example, with reference back to FIG. 6, the sensor 200 can be configured to include additional regions associated with red, green and blue filters. Using known image processing techniques, the eyes can be identified as pupils surrounded by irises surrounded by the whites of the eyes surrounded by skin tone. In an embodiment in which the light sources 103 and 105 are infrared light sources, the results obtained using visible light can be compared against results obtained using differential angle illumination with the infrared lights, providing an even higher level of confidence in the accuracy of the imaging information.

The differential illumination angle technique can be applied in a different way towards the objective of biometric detection. In some applications, feature recognition depends on knowledge of orientation of the subject. By highlighting the pupils, differential illumination allows determination of the horizontal axis of a face. This information can be used to orient images of such features as irides and faces for comparison to databases for biometric identification, for example.

In one embodiment, eye location can first be detected using one of the methods described above. A sub-region of the imager can then be identified around the eyes. Subsequent images can be collected from this sub-region only, thereby speeding image processing and frame rate. Alternatively, this location information can be used to direct a second (higher-resolution) detector (imager). For example, a first (lower-resolution) detector can be used to locate the eye as described above, then the second (higher-resolution) detector can be used to focus in on and monitor the eye. This pointing concept can be applied to a wide range of applications, not just iris detection.

Accumulation of Results to Determine Drowsiness

According to the various embodiments of the invention, a determination can then be made with regard to the drowsiness (or conversely, the wakefulness) of the vehicle operator. For example, the amount of time that the eyes are open can be measured and compared against a predetermined threshold. Failure to satisfy that threshold would indicate that the eye(s) have been closed (or nearly closed) for a prolonged period, suggesting that the operator is falling asleep and perhaps triggering an alert that would startle the operator into wakefulness.

Handling Images

One or more of several features may be incorporated into detector 101 of FIG. 1. The images captured by detector 101 are, in general, not going to be displayed, for example, on a display screen or as a printed picture. Thus, although the discussion pertaining to FIGS. 2A–2C infers the generation of images, in actuality these images reside in some portion of the memory of detector 101 or on sensor 200 (FIG. 6), in a form suitable for processing (differencing) as described above, and not necessarily in a form suitable for viewing. Also, the images may reside in memory or on sensor 200 only long enough for processing, after which the images may be discarded or overwritten. For example, in the case of sequential imaging, only one or two consecutive images, or only the images captured in a burst (as discussed above), may be stored at any one time. Accordingly, the memory requirements for detector 101 can be reduced. In the case of simultaneous imaging, the detector can be operated in single-shot mode, where only one image is collected, rather than video mode. This approach has the additional advantages of allowing easy access to raw pixel data for pixel-based image processing while preserving the ability (if needed) to transmit images over relative slow buses.

In addition, according to the embodiments described above, the pupil is located by taking the difference between two images; this differencing process is repeated. The processing can be generally summarized as determining whether or not a bright spot exists in the differential image. Rather sophisticated processing techniques are available for analyzing images; however, these processes do not need to be used. Consequently, the processing requirements for detector 101 can be reduced. In addition, because of the repetitiveness of the processing, a customized processor (such as an application specific integrated circuit or the like) can be utilized by detector 101. Alternatively, for CMOS detectors, the image processing may be performed on the same chip as the sensor. In any of these cases, image processing can be accomplished quickly and inexpensively.

Symmetric Illumination to Reduce Shadowing

Figure 11:
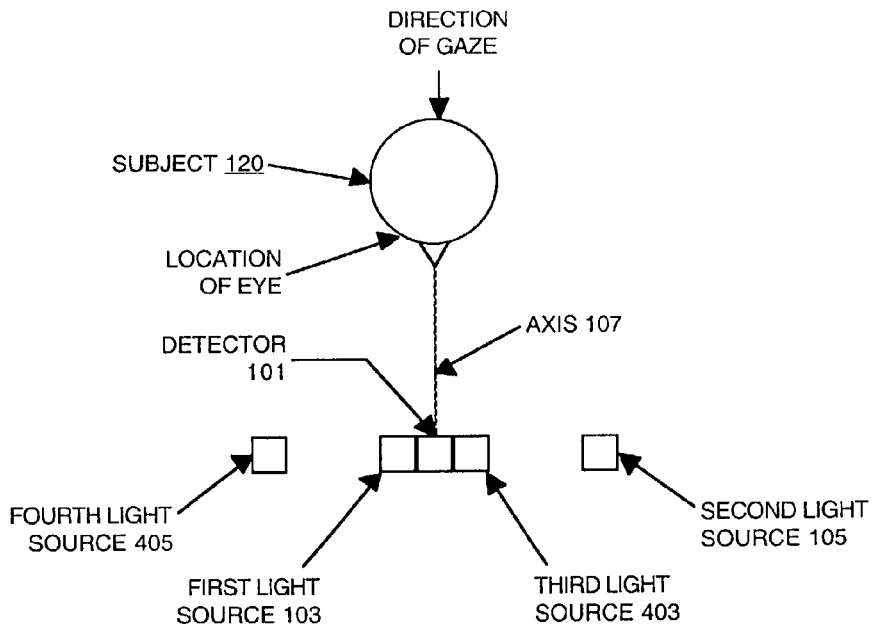
FIG. 11 is a block diagram of another embodiment of an apparatus for pupil detection in accordance with the invention.

FIG. 11 is a block diagram of another embodiment of an apparatus for pupil detection in accordance with the invention. In this embodiment, relative to the preceding embodiments, a third light source 403 and a fourth light source 405 are added. In various other embodiments, the apparatus of FIG. 11 may incorporate some or all of the features described above. The use of additional light sources can help reduce shadowing and attendant effects.

In one embodiment, third light source 403 uses the same wavelength as first light source 103, and fourth light source 405 uses the same wavelength as second light source 105. In one embodiment, the first light source 103, the second light source 105, the third light source 403, and the fourth light source 405 emit light that is substantially equal in intensity (brightness). In one embodiment, the first and third light sources 103 and 403 are equidistant from the axis 107 and in the same plane perpendicular to the axis 107; that is, they are symmetric about the axis 107. In another embodiment, the second and fourth light sources 105 and 405 are equidistant from the axis 107 (symmetric about the axis 107). In one embodiment, first light source 103 and third light source 403 are situated at a same (first) illumination angle, and second light source 105 and fourth light source 405 are situated at a same (second) illumination angle (different from the first).

Detecting Pupil Diameter

Figure 12:
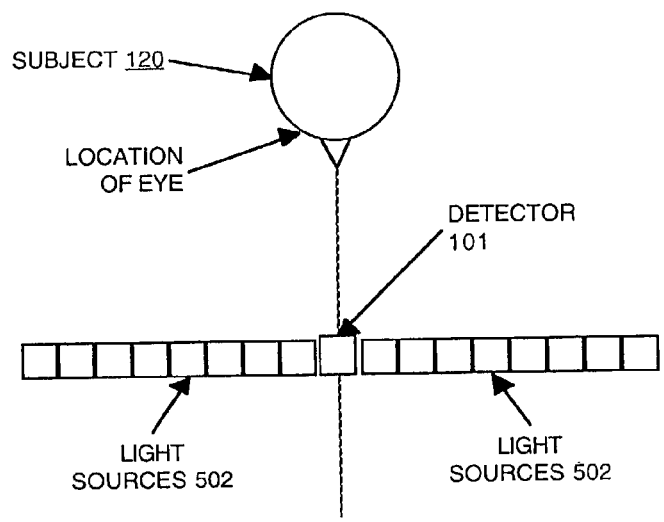
FIG. 12 is a block diagram of an embodiment of an apparatus for detecting pupil diameter in accordance with the invention.

FIG. 12 is a block diagram of an embodiment of an apparatus for detecting pupil diameter in accordance with the invention. Because the pupil causes light incident on it to be reflected back by the retina toward the direction from which the light came, a larger pupil diameter should permit reflections to be captured at a larger angle from the source. In the embodiment of FIG. 12, a series of light sources 502 is placed on each side of the detector 101 as shown. The light sources 502 can be illuminated sequentially to determine an illumination angle at which the retinal return is no longer visible to detector 101 or is substantially reduced. The size of the pupil can then be derived according to which of the light sources 502 provided a measurable retinal return. For example, the size of the pupil can be inferred by identifying the light source furthest from the detector 101 that caused a non-negligible retinal return to be provided to the detector 101.

Alternatively, the size of the pupil can be estimated using profiles of the intensity of the retinal return signal (the signal generated by the detector 101 of FIG. 1) versus illumination angle. For various pupil diameters, a profile of signal intensity versus illumination angle can be derived. The retinal return signals obtained by sequentially illuminating the light sources 502 can be compared against the various profiles to estimate pupil diameter. Pupil diameter can also be estimated by measuring the diameter of the bright spot captured in the differential image (e.g., by measuring the diameter of the bright spot 310 of FIG. 2C).

With reference to FIG. 12, the images captured by detector 101 over time can be used to check that neither the head nor the eye has moved enough to invalidate the measurement of pupil diameter. Using rapid scan rates and frame rates, brief contractions of the pupil can be captured. Some studies show that brief contractions of the pupils can be used to determine whether someone is not being truthful; therefore, by measuring pupil diameter, embodiments in accordance with the invention may be utilized as lie detectors.

Eye Detection with a Single Source

Figure 13:
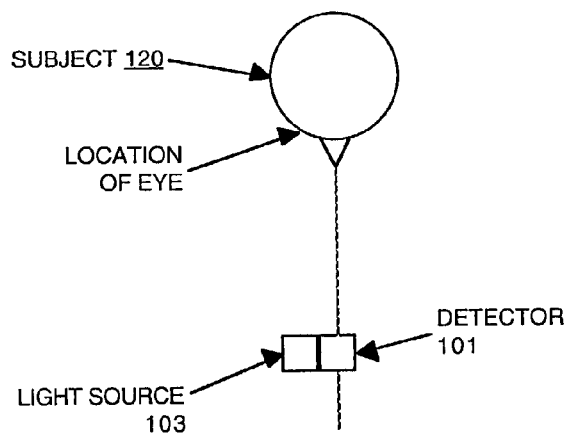
FIG. 13 is a block diagram of still another embodiment of an apparatus for pupil detection in accordance with the invention.

FIG. 13 is a block diagram of still another embodiment of an apparatus for pupil detection in accordance with the invention. In this embodiment, a single detector 101 and a single on-axis light source 103 are utilized.

Figure 14:
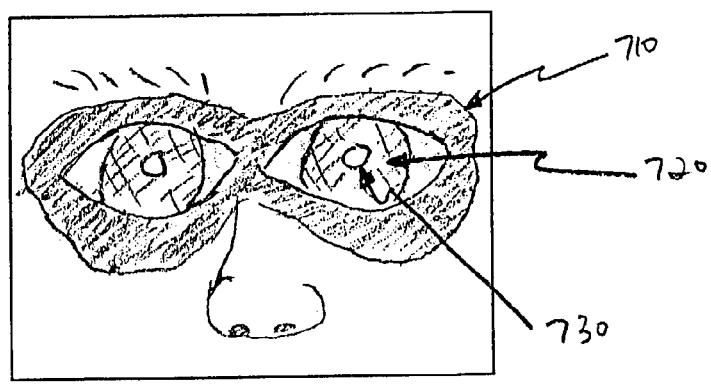
FIG. 14 illustrates one embodiment of a technique for detecting the pupils of a subject's eyes using the apparatus of FIG. 6 in accordance with the invention.

FIG. 14 illustrates one embodiment of a technique for detecting the pupils of a subject's eyes using the apparatus of FIG. 13 in accordance with the invention. Under on-axis illumination, the eyes of a subject are distinct from the background, appearing as bright spots 730 surrounded by darker regions 710 and 720. In this manner, the pupils (corresponding to bright spots 730) can be detected without capturing an off-axis image, and without the subsequent differencing of the on-axis and off-axis images.

In another embodiment, an image sensor would comprise filters, for example in a checkerboard pattern, that are designed to discriminate between light from a single (on-axis) source and ambient background light. This approach allows simultaneous, approximate background subtraction.

Combining Techniques

A number of different embodiments have been described for drowsiness detection apparatus that are used to detect the pupils of a subject's eyes. The various features of the different embodiments may be used alone or in combination.

Location of Drowsy Driver Detector

Based on whether or not the pupils are detected, it can be inferred whether or not the subject is falling asleep, for example. The various embodiments in accordance with the invention accomplish this without physically contacting the subject and over a range of distances and angles. As such, flexibility is afforded in the packaging of the apparatus and in the placement of the apparatus within the motor vehicle. In practice, the location of the apparatus may be selected to minimize interference from sunlight and glare. In an automobile, for example, the apparatus could be located in the following locations:

on the dashboard where the speedometer and other such gauges are located;

in a stereo panel, packaged with other audio equipment that can be selected by a customer in place of standard equipment—this would allow the apparatus to be backfit to older vehicles; the sensor could be connected to transmitting or receiving devices already present in the audio equipment; and the audio equipment could be utilized to provide an audible alert to the driver;

on the upper portion of the steering wheel;

on the rear view mirror;

in or behind the rear view mirror (e.g., light is emitted through a mirror that acts as a filter that reflects visible light and transmits infrared light, so that light reflected from the retinas can pass through the mirror to the detector);

on the top of the dashboard, using reflection off of the windshield;

in the molding of the window frame;

in the windshield itself;

in a separate module mounted on the center console or in other places where controls and equipment, such as air conditioning controls, may be located;

on the top of the windshield or at the front of the roof; or integrated with an on-board navigation system.

Enhancing Eye Detection Results

Additional features may be incorporated into the drowsiness detection apparatus to further improve the accuracy of the image analysis. For example, image processing techniques based on the correlation between on-axis and off-axis images can be used to determine relative motion in those embodiments in which images are captured at different times. If the magnitude of the motion is too high, based on some measurable threshold, then the associated information can be ignored (discarded) and an error message can be sent to the processor.

Another feature that can be employed is to couple to the apparatus, or incorporate within the apparatus, accelerometer(s) or some other type(s) of device(s) (e.g., an infrared or radar imager that looks outside of the motor vehicle) that can be used to determine whether the automobile is in motion or accelerating. The vehicle speedometer can also be coupled to the apparatus. If the vehicle is not moving, the operator alert mechanism can be disabled. The accelerometer or similar device can also be used to determine if excessive motion might be expected due to rapid acceleration.

Image processing techniques such as histograms or that use photosensitive devices can be used to determine whether overall (ambient) light levels are too high or too low to be reliable. This information can be used to determine whether to enhance the robustness of the detector or of the light sources; this is described further in conjunction with step 840 of FIG. 15, below. Image processing techniques can also be used to validate whether the bright spot in the differential image is the pupil, by ascertaining whether or not the bright spot is of the right size, shape or position.

Method for Pupil Detection

Figure 15:
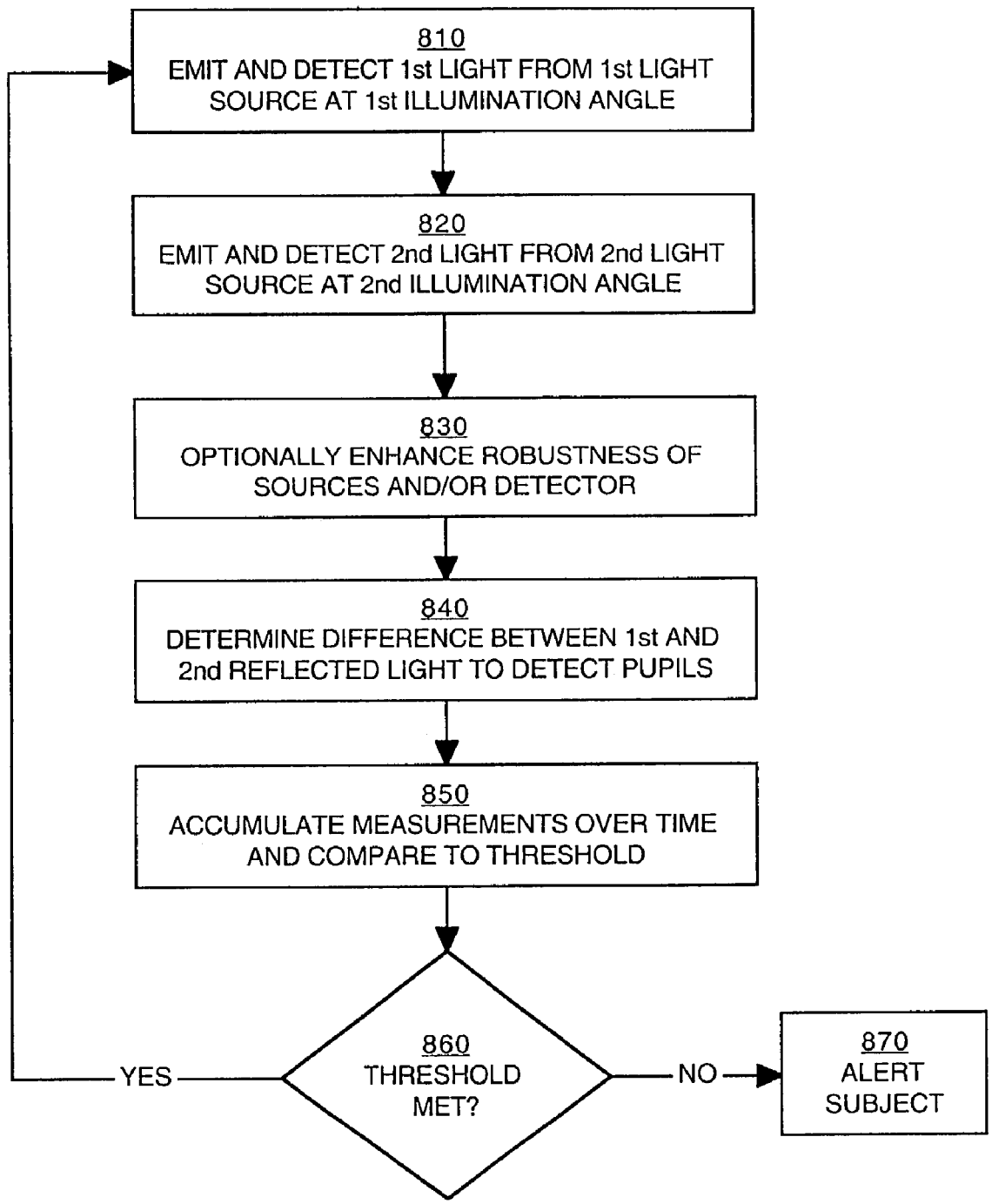
FIG. 15 is a flowchart of a method for pupil detection according to one embodiment in accordance with the invention.

FIG. 15 is a flowchart of a method for pupil detection according to one embodiment in accordance with the invention. Although specific steps are disclosed in flowchart 800, such steps are exemplary. That is, embodiments in accordance with the invention are well suited to performing various other steps or variations of the steps recited in flowchart 800. It is appreciated that the steps in flowchart 800 may be performed in an order different than presented, and that not all of the steps in flowchart 800 may be performed.

In step 810, in the present embodiment, first light is emitted from a first light source at a first illumination angle relative to the axis of a detector. In one embodiment, the first light is emitted by multiple light sources symmetrically located about the axis (equidistant from the axis). Reflected first light is received at the detector.

In step 820, in the present embodiment, second light is emitted from a second light source at a second illumination angle relative to the axis of a detector. The second illumination angle is greater than the first illumination angle. In one embodiment, the second light is emitted by multiple light sources with substantially similar illumination angles. Reflected second light is received at the detector.

For purposes of the present application, "substantially similar illumination angles" is defined as follows. It is desirable for the multiple off-axis light sources to be in the range of approximately 3 to 15 degrees (refer to the discussion of FIG. 1). The lower limit is far enough off-axis not to get appreciable retinal return (red-eye). The upper limit is chosen so that the on-axis and off-axis views have similar illumination patterns, such as shadowing. As stated above, for the subtraction of the off-axis view from the on-axis view effectively to cancel scene details in regions away from the retinas, it is desirable that the two scene views appear nominally identical. There may also be an overall device size constraint that limits the upper off-axis angle limit.

In one embodiment, the first and second lights have substantially equal wavelengths. In such an embodiment, the first and second light sources are alternately actuated (illuminated). For purposes of the present application, "substantially equal wavelengths" is defined as follows. For clean image subtraction, it is desirable that the apparent on-axis and off-axis brightness be nominally the same except in the retinas. The apparent brightness can change with wavelength dependencies in either the detector's sensitivity and/or scene reflectance. Furthermore, interfering illumination sources such as streetlights may have different spectra. This effect cannot be corrected by digitally scaling one or both images. Therefore, the wavelengths need to be similar enough not to experience a significant difference in detector sensitivity or scene reflectance.

In another embodiment, the first and second lights have wavelengths that are different. When using different wavelengths, they should be far enough apart to minimize wavelength overlap either (a) in the source illumination, and/or (b) in the overall detector sensitivity (including any filtering). In such an embodiment, the first and second light sources are actuated (illuminated) at substantially the same time.

For purposes of the present application, "substantially the same time" is defined as follows. To minimize motion artifacts in sequentially-captured difference images, it is desirable that the two views of the scene be captured close in time. Ideally, the two views are captured simultaneously, eliminating this source of motion artifacts. There is no distinct cutoff for an acceptable delay; the closer to "simultaneous" the better. Practical limitations include effective frame rate, and synchronization errors. For simultaneous capture, motion artifacts can be limited by utilizing the same exposure time for both wavelengths.

In yet another embodiment, the first light and the second light are of substantially equal intensity (brightness). For purposes of the present application, "substantially equal intensity" is defined as follows. The off-axis illuminated image is subtracted from the on-axis-illuminated image. Except for the retinas, the remainder of the image detail should nominally cancel. This requires that the pixel levels in the two images be similar, except for the retinas. Balancing the pixel levels of the two images through exposure times or by digitally scaling one or both images is ultimately constrained by noise and saturation effects, so it is advantageous to balance pixel signal levels from areas other than the retinas (e.g., cheeks) optically.

In an embodiment in which the first and second light sources are alternately actuated, the reflected first light and the reflected second light are captured by the detector in consecutive frames. In an embodiment in which the first and second light sources are actuated essentially at the same time, the reflected first light and the reflected second light are filtered and captured by the detector using a sensor that is configured to capture both sub-frames (refer to the discussion of FIG. 6, above). The detector simultaneously captures a first sub-frame corresponding to the reflected first light and a second sub-frame corresponding to the reflected second light, and the difference is determined from these sub-frames. As described above, in other embodiments, multiple detectors can be used in a redundant manner. Other features and enhancements have been described above and are not repeated here.

In step 830 of FIG. 15, in one embodiment, the robustness of the approaches described herein can be enhanced using a variety of techniques. For example, during daylight hours, the intensity of the light (emitted or reflected) may be dim in comparison to sunlight. Even at night, other light sources (e.g., headlights, streetlights, etc.) can make it more difficult to capture the reflected light. In order to make the apparatus more robust under the various lighting conditions that may exist, various mechanisms may be used, alone or in combination. These mechanisms may be "always on" or they may be implemented (automatically or manually) according to ambient light conditions. For example, ambient light conditions can be monitored, and when the amount (e.g., brightness) of the ambient light exceeds a threshold, one or more of the mechanisms described below can be implemented accordingly.

MODULATION. In one embodiment, a modulation may be imparted on a signal of interest (e.g., the retinal return signal) in order to distinguish it from interference and noise. In one such embodiment, a synchronous (lock-in or phase sensitive) detection approach is applied to enhance single channel signals. In general, in a synchronous detection approach, a light source (for example, a laser) is passed through what is commonly referred to as a chopper, which modulates the light at a selected frequency. Direct electrical modulation of certain light sources, including semiconductor light-emitting diodes, is also possible. The synchronization output of the chopper, modulated at the selected frequency, is input to a lock-in amplifier. The signal received by the detector (e.g., the retinal return signal) is also input into the lock-in amplifier. The lock-in amplifier mixes the synchronization output of the chopper with the optically detected signal. A narrow band filter (around the selected frequency) is applied, yielding a signal at about the selected frequency. As a result, a signal that may be otherwise difficult to distinguish against the noise becomes much more distinguishable. Here, it is desirable to avoid collecting data (except for noise measurements) when the signal of interest is not present. This can be accomplished either by modulating detector sensitivity, by appropriate clocking of the detector, by using shutters, or by other means. As an illustrative example, an on-axis image can be taken with LEDs on ($I_{11}$), then with LEDs off ($I_{10}$). An off-axis image can be taken with LEDs on ($I_{01}$) and with LEDs off ($I_{00}$). The final differential image would be ($I_{11}-I_{10}$)-($I_{01}-I_{00}$); the difference would be due to modulation.

An alternative approach for enhancing single channel signals is to emit a temporally coded sequence rather than a single probe pulse and correlate this pattern with the return signal. For example, Golay codes can be used to enhance the signal-to-interference ratio and thus reduce integration time for a measurement. In essence, the sensitivity of the detector can be modulated. Alternatively, pattern coding can be done by modulating the illuminated region of the subject with, for example, a scanning laser point or line that is synchronized with the sensor. In this way, signals from illuminated regions can be compared with background illumination of the subject with high spatial resolution.

INCREASING ILLUMINATION INTENSITY. In another embodiment, the intensity of the first and second lights can be increased (perhaps only under brighter ambient conditions) to provide a stronger test signal, up to maximum limits for eye safety.

NARROWING SPECTRAL RANGE FOR DETECTION. In another embodiment, spike filters can be used to narrow the spectral range received by the detector to the wavelengths associated with the light sources, to better filter out ambient light and other interfering signals.

In yet another embodiment, the spectral range of the light sources can be narrowed using a resonant cavity LED or a laser such as a VCSEL as the light source. With a matching spike filter, the signal captured by the detector will be stronger in comparison to ambient light within the spectral band collected. In principle, a narrow enough wavelength bandwidth is expected to allow the return signals to exceed solar radiation because infrared exposure levels from the sun are under maximum permissible exposure limits. If the narrow bandwidth source casts a beam too narrow spatially for eye safety purposes, the beam can be spread using diffractive lenses or diffusers, for example. Using a VCSEL light source has the additional advantages of narrow spectral extent and considerably smaller shift in wavelength with temperature compared to typical LEDs.

NARROWING ANGULAR RANGE FOR ON-AXIS ILLUMINATION. In one more embodiment, the angle of illumination of the on-axis light source can be reduced by using a beam splitter to illuminate the source co-linearly with the normal to the detector. Alternatively, the size of the detector can be reduced to the extent practical, and/or the detector can be located as far as possible from the subject. As another alternative, baffles can be placed between the on-axis light source and the detector. In yet another alternative, the light source(s) and the detector can be integrated on the same substrate using various bonding techniques, for example, those that employ solder. Higher degrees of integration may be used. Numerous other physical layouts are possible, including those in which the emitters are not in the same plane as the imager, for example.

NARROWING ANGULAR RANGE FOR DETECTION. In one embodiment, the angle of collection of the detector can be reduced using collimating barriers, optics, and/or pinholes to block light from other sources that might otherwise be captured by the detector. The detector's field of view can be kept wide enough to view both pupils under a range of circumstances, while still allowing some (most) signals from interfering sources to be blocked. The collection angle can also be reduced by using only a subset of the pixels on the sensor device, in which only those pixels that view the pupils and nearby regions are used after the pupils have been identified. Alternatively, two sensors can be integrated, one to identify the location of the pupils, and the other having a smaller collection angle than the first. The second sensor is aimed using information gained from the first sensor. The second sensor can then obtain a higher spatial resolution. This second sensor may be positioned using small actuators in order to aim it at the subject's eyes.

REDUCING DEPTH OF FIELD. In another embodiment, the depth of field of the detector can be decreased, such that the pupils will be in focus while more distant interfering light sources are not in focus. If the more distant light sources are blurred, the images used for differencing will contain less distinct features, which are more readily distinguishable from the retinal return.

CHOOSING OPERATING WAVELENGTH TO REDUCE SOLAR INTERFERENCE. In another embodiment, shorter wavelength light sources can be used. In an automotive application, inherent short wavelength (particularly ultraviolet) absorption in windshield glass and coatings deposited on the windshield significantly reduce the amount of ultraviolet light from the sun that can impinge on the driver. Therefore, operating in this region can improve the signal-to-interference performance. In addition, due to the presence of various pigments in the retina that absorb in the blue to ultraviolet region, eye detection can be done based on the absorption characteristics of the light source. Alternatively, the windshield glass can be coated to aid in the blocking of outside light sources, particularly in the infrared range.

UTILIZING FACIAL RECOGNITION AT HIGH LIGHT LEVELS. In one more embodiment, at night or under other conditions in which ambient light is sufficiently low in level, pupils can be located as described herein, while under conditions when the level of ambient light is high, more conventional facial recognition techniques can be used to locate the eyes and to determine whether the eyes are open or closed (or nearly closed).

INTENTIONAL SATURATION. In yet another embodiment, the exposure time of the detector can be adjusted to allow longer exposures in lower lighting conditions; however, the exposure is not shortened for brighter conditions. As a result, under brighter lighting conditions, the image may be saturated (over-exposed); however, the present concern is not with the quality of the image but with the detectability of the pupils within the image. Even with the image saturated, the bright spots associated with the pupils should still be detectable unless flare or blooming effects become excessive. Baffles can be employed in the optical system to reduce flare, and anti-blooming silicon imager features can be used as well.

In step 840 of FIG. 15, in the present embodiment, the difference between the reflected first and second light received by the detector is determined. When the eyes are open, the difference will include a bright spot; when the eyes are closed or nearly closed, the bright spot will be absent. In one embodiment, the differencing is performed by an image processor coupled to the detector. In another embodiment, the differencing is performed by an image processor incorporated into the drowsiness detection apparatus. In one such embodiment, the differencing is performed using the sensor device utilized with the detector.

In steps 850, 860 and 870, in the present embodiment, a state of drowsiness or wakefulness (or, conversely, alertness) can be determined by measuring the amount of time that the eyes are closed (or nearly closed, or frequently blinking) or open, and optionally by measuring the area of the reflected signal compared to the area of the pupil. In step 850, in one embodiment, a running average of the amount of time that the eyes are closed (or nearly closed) is accumulated. In step 860, the running average from step 850 can be compared against a threshold, specified in advance, and used for indicating whether the eyes are closed (or nearly closed) for an excessive amount of time.

If the threshold is not met, the subject (e.g., the vehicle operator) can be alerted (step 870). In one embodiment, this is accomplished using a control system that can be either incorporated into the drowsiness detection apparatus or coupled to it. Based on a specified threshold (e.g., as described above), or a similar type of methodology, the control system can actuate an alarm. The alarm may be audible, or it may take other forms designed with the intent of alerting the subject. If the threshold is met, then flowchart 800 can return to step 810.

Alternatively, another type of measurement may be additionally employed, and results from this other measurement can be additionally employed in step 870. For example, measurements from a lane change detector may be used in conjunction with the drowsiness detection apparatus, or vice versa, in order to provide a greater degree of confidence that an alert or some other form of protective action is appropriate.

Summary

In summary, the invention provides, in various embodiments, pupil detection apparatus and methods thereof. The locations of pupils as well as the amount of time that the eyes are open/closed/nearly closed can be determined in a non-invasive manner, without making physical contact with the subject. Pupils/drowsiness can be detected both in the dark and in the presence of background light at various levels, including bright light Pupils/drowsiness can be detected for stationary subjects as well as moving subjects and backgrounds. The apparatus, in its various embodiments, can be located in a variety of locations relative to the subject. The use of infrared light in some embodiments will not interfere with the subject's night vision, and is invisible to most people. Setup and operation is simple, and the cost is low.

Besides drowsiness detection, embodiments in accordance with the invention can be used to: monitor the onset or the end of sleep; detect drowsiness in venues other than motor vehicles; detect the level of attentiveness of a subject, the presence of a subject, the location of a subject; locate the pupils for iris identification techniques; or measure pupil size. Other applications include lie detection and ophthalmology. Applications also include eye-based and facial-based biometric applications, such as eye or facial based identification applications including retinal detection and iris detection, or for distinguishing a live subject from an image of the subject. Applications may also include those for animal subjects.

The invention is thus described in various embodiments. While the invention has been described in particular embodiments, it should be appreciated that the invention should not be construed as limited by such embodiments, but rather construed according to the following claims.

What is claimed is:

1. An apparatus for pupil detection, said apparatus comprising:
   - a first detector for receiving reflected light;
   - a first light source for emitting first light at a first illumination angle relative to the axis of said first detector;
   - a second light source for emitting second light at a second illumination angle relative to said axis, said second illumination angle greater than said first illumination angle, said first light and said second light having substantially equal intensity;
   - wherein pupils of a subject's eyes are detectable using the difference between reflected first light and reflected second light received at said first detector; and
   - a plurality of additional light sources that are sequentially illuminated to measure pupil diameter.

2. The apparatus of claim 1 further comprising:
   - a third light source for emitting third light at substantially a same wavelength as said first light, said first and third light sources symmetrically located about said axis; and
   - a fourth light source for emitting fourth light at substantially a same wavelength as said second light, said second and fourth light sources symmetrically located about said axis.

3. The apparatus of claim 1 wherein said first light and said second light have wavelengths that are substantially equal, wherein said first and second light sources are alternately activated.

4. The apparatus of claim 1 wherein said first detector captures reflected first light and reflected second light in consecutive frames, wherein said difference is determined from pairs of consecutive frames.

5. The apparatus of claim 1 wherein said first light and said second light have wavelengths that are different, wherein said first and second light sources are activated substantially at a same time.

6. The apparatus of claim 5 wherein said first light has a wavelength shorter than said second light.

7. The apparatus of claim 5 wherein said first detector comprises filters for differentiating between said reflected first light and said reflected second light, wherein said first detector captures a first sub-frame corresponding to said reflected first light and a second sub-frame corresponding to said reflected second light, wherein said difference is determined using said first and second sub-frames.

8. The apparatus of claim 7 wherein said first and second lights are infrared or near-infrared lights, wherein said first detector further comprises filters for distinguishing visible light from said reflected first and second lights, and wherein said first detector also captures a frame corresponding to said visible light.

9. The apparatus of claim 5 wherein said first detector comprises a first filter for blocking visible light and a second filter that blocks reflected first light.

10. The apparatus of claim 5 wherein reflected first light and reflected second light are captured in a single image.

11. The apparatus of claim 5 wherein said first detector comprises filters for differentiating between said reflected first light and said reflected second light, wherein said filters are configured so that a first pixel of said first detector receives first light and a second pixel adjacent to said first pixel receives second light.

12. The apparatus of claim 1 wherein said first light is polarized in one direction and said second light is polarized in a different direction.

13. The apparatus of claim 12 wherein said first detector comprises filters for differentiating between first polarized light and second polarized light.

14. The apparatus of claim 13 wherein said filters are configured so that a first pixel of said first detector receives first polarized light and a second pixel adjacent to said first pixel receives second polarized light.

15. The apparatus of claim 13 wherein said filters comprise semi-transparent material.

16. The apparatus of claim 1 further comprising a second detector.

17. The apparatus of claim 16 wherein said second detector has a smaller collection angle than said first detector, wherein said second detector is aimed using information from said first detector.

18. The apparatus of claim 16 wherein said second detector has a higher resolution than said first detector, wherein said second detector is aimed using information from said first detector.

19. The apparatus of claim 16 further comprising wavelength-selective filters positioned such that said first detector receives said reflected first light and said second detector receives said reflected second light.

20. The apparatus of claim 1 further comprising a beam splitter.

21. The apparatus of claim 1 wherein said first illumination angle ranges from approximately zero to three (3) degrees and wherein said second illumination angle ranges from approximately 3 to 15 degrees.

22. The apparatus of claim 1 wherein said first and second lights are emitted in timed bursts, said bursts separated by time intervals that are longer than said bursts.

23. The apparatus of claim 1 wherein said first and second lights are modulated to distinguish them from ambient conditions.

24. The apparatus of claim 1 wherein the intensity of said first and second lights is increased according to ambient light conditions.

25. The apparatus of claim 1 wherein a spectral range associated with said first and second lights is narrowed according to ambient light conditions.

26. The apparatus of claim 1 wherein said reflected first light and said reflected second light are filtered with a spike filter to filter out ambient lighting.

27. The apparatus of claim 1 wherein a collection angle of said detector is reduced according to ambient light conditions, wherein reducing said collection angle reduces collection of ambient light.

28. The apparatus of claim 1 wherein a depth of field of said detector is reduced, wherein said pupils are substantially in focus while objects more distant than said pupils are of reduced focus.

29. The apparatus of claim 1 wherein a wavelength for said first light and a wavelength for said second light that are different from dominant wavelengths of ambient light are selected.

30. The apparatus of claim 1 wherein an exposure time of said detector for a lower amount of ambient light is determined and wherein said exposure time is maintained with an increase in ambient light.

31. The apparatus of claim 1, used for drowsiness detection.

32. The apparatus of claim 1, used for lie detection.

33. The apparatus of claim 1, used for distinguishing between a live subject and an image of said subject.

34. The apparatus of claim 1, used for eye-based identification.

35. The apparatus of claim 1, used for facial-based identification.

36. The apparatus of claim 1 wherein said first detector comprises a mosaic of visible and infrared filters.

37. The apparatus of claim 1 wherein said first detector comprises a mosaic of infrared filters.

38. The apparatus of claim 1 wherein at least one of said first and second light sources is a vertical cavity surface-emitting laser.

39. A method for pupil detection, said method comprising:
emitting first light from a first light source at a first illumination angle relative to the axis of a detector;
emitting second light from a second light source at a second illumination angle relative to said axis, said second illumination angle greater than said first illumination angle, said first light and said second light having substantially equal brightness;
receiving reflected first light and reflected second light at said detector;
determining the difference between said reflected first light and said reflected second light, wherein pupils of a subject's eyes are detectable from said difference;
receiving reflected light from a plurality of additional light sources that are sequentially illuminated; and
determining pupil diameter using said reflected light.

40. The method of claim 39 further comprising:
polarizing said first and second lights.

41. The method of claim 39 further comprising:
emitting third light from a third light source, said third light at substantially a same wavelength as said first light, said first and third light sources symmetrically located about said axis; and
emitting fourth light from a fourth light source, said fourth light at substantially a same wavelength as said second light, said second and fourth light sources symmetrically located about said axis.

42. The method of claim 39 wherein said first light and said second light have wavelengths that are substantially equal, wherein said first and second light sources are alternately actuated and wherein said detector captures reflected first light and reflected second light in consecutive frames.

43. The method of claim 39 wherein said first light and said second light have wavelengths that are different, wherein said first and second light sources are actuated substantially together and wherein said detector filters said reflected first light and said reflected second light using respective filters to capture a sub-frame corresponding to said reflected first light and a sub-frame corresponding to said reflected second light.

44. The method of claim 39 wherein said first and second lights are emitted in timed bursts, said bursts separated by time intervals that are longer than said bursts.

45. The method of claim 39 further comprising:
determining whether said subject is drowsy or alert.

46. The method of claim 39 further comprising:
determining whether said subject is lying or truthful.

47. The method of claim 39 further comprising:
distinguishing between a live subject and an image of said subject.

48. The method of claim 39 further comprising:
applying an eye-based identification technique subsequent to detection of said pupils.

49. The method of claim 39 further comprising:
using detection of said pupils to determine facial orientation.

50. An apparatus for pupil detection, said apparatus comprising:
a first detector for receiving reflected light;
a first light source for emitting first light at a first illumination angle relative to the axis of said first detector;
a second light source for emitting second light at a second illumination angle relative to said axis, said second illumination angle greater than said first illumination angle, said first light and said second light having substantially equal intensity;
wherein pupils of a subject's eyes are detectable using the difference between reflected first light and reflected second light received at said first detector; and
a series of adjacent additional light sources that are positioned at different illumination angles and that are sequentially illuminated to measure pupil diameter, wherein measuring pupil diameter comprises comparing retinal return to the illumination angles of the light sources.

51. A method for pupil detection, said method comprising:
emitting first light from a first light source at a first illumination angle relative to the axis of a detector;
emitting second light from a second light source at a second illumination angle relative to said axis, said second illumination angle greater than said first illumination angle, said first light and said second light having substantially equal brightness;
receiving reflected first light and reflected second light at said detector;
determining the difference between said reflected first light and said reflected second light, wherein pupils of a subject's eyes are detectable from said difference;
receiving reflected light from a series of adjacent additional light sources that are positioned at different illumination angles and that are sequentially illuminated; and
determining pupil diameter using said reflected light, wherein determining pupil diameter using said reflected light comprises comparing retinal return to the illumination angles of the light sources.

* * * * *